(12) United States Patent
Sharpe

(10) Patent No.: US 7,677,197 B2
(45) Date of Patent: Mar. 16, 2010

(54) TREATMENT OF TISSUE SPECIMENS

(75) Inventor: James Alexander Sharpe, Edinburgh (GB)

(73) Assignee: Medical Research Council, London (GB)

( * ) Notice: Subject to any disclaimer, the term of this patent is extended or adjusted under 35 U.S.C. 154(b) by 567 days.

(21) Appl. No.: 10/518,307

(22) PCT Filed: Jun. 13, 2003

(86) PCT No.: PCT/GB03/02570

§ 371 (c)(1),
(2), (4) Date: Sep. 26, 2005

(87) PCT Pub. No.: WO2004/003129

PCT Pub. Date: Jan. 8, 2004

(65) Prior Publication Data

US 2006/0105332 A1    May 18, 2006

(30) Foreign Application Priority Data

Jun. 27, 2002   (GB) .................................. 0214846.8
Nov. 27, 2002   (GB) .................................. 0227649.1

(51) Int. Cl.
*B05C 3/00*   (2006.01)

(52) U.S. Cl. ...................................... 118/423; 118/429
(58) Field of Classification Search ................. 118/423, 118/429; 422/104, 64, 99; 366/317, 286; 436/63, 174, 176
See application file for complete search history.

(56) References Cited

U.S. PATENT DOCUMENTS

| | | | | | |
|---|---|---|---|---|---|
| 2,583,379 | A | * | 1/1952 | Kling | 118/416 |
| 3,062,225 | A | * | 11/1962 | Mans | 134/69 |
| 4,202,289 | A | * | 5/1980 | Bils | 118/50 |
| 6,355,104 | B1 | * | 3/2002 | Polster | 118/666 |
| 6,562,136 | B1 | * | 5/2003 | Chappa et al. | 118/500 |

* cited by examiner

*Primary Examiner*—Brenda A Lamb
(74) *Attorney, Agent, or Firm*—Barnes & Thornburg LLP

(57) ABSTRACT

Apparatus for treating tissue specimens comprises a stationary outer casing (2) in the top of which is positioned an annular trough (3) for holding a liquid. Rotatably mounted in the outer casing (2) is a central hub (5) supporting a disc-like lid (6) the underside of which carries a magnet (7). In use, the magnets hold, in a detachable manner, tissue specimens (12) and the trough (3) is filled with a liquid for treating the specimens. The hub (5) is capable of vertical translational movement with respect to the casing (2) to enable the specimens to be lowered into and subsequently lifted out of the trough (3). A method of treating tissue specimens is also provided.

5 Claims, 2 Drawing Sheets

TREATMENT OF TISSUE SPECIMENS

FIELD OF THE INVENTION

This invention relates to the treatment of tissue specimens, particularly (but not exclusively) prior to imaging of the specimens by optical projection tomography (OPT), and to uses of optical projection tomography methods and apparatus.

BACKGROUND TO THE INVENTION

Tissue specimens are normally treated by immersion in one or more liquids, before the specimens are imaged in OPT apparatus, and the invention was devised as a way of facilitating this pre-treatment of specimens.

SUMMARY OF THE INVENTION

According to one aspect of the invention there is provided apparatus for treating tissue specimens by immersion in a liquid, the apparatus comprising a first structure providing a chamber for holding the liquid, and a second structure including holding means for releasably holding the specimens, the first and second structures being relatively moveable in a direction having a vertical component between a first position in which the holding means are relatively close to the chamber and in which the second structure closes the top of the chamber to enable the specimens to be immersed in the liquid whilst the latter is protected from the environment, and a second position in which the holding means are relatively distant from the chamber to enable the specimens to be loaded onto or unloaded from the holding means.

Preferably, the first structure is stationary and the second structure is shiftable vertically with respect to the first structure.

The holding means may include magnets to enable specimens, each provided with a metal mount, to be detachably retained on the second structure by magnetic attraction.

The chamber is preferably in the form of an annular trough in which case the holding means may hold the specimens so that the latter depend from the holding means, conveniently at angularly spaced positions around a circle such that the specimens are lowered into the trough as the second structure is lowered to its first position. In this case, the second structure preferably includes a lid which acts to close the chamber in the first position and the underside of which carries the holding means. Lid closure helps to prevent evaporation of volatile treatment liquids.

The second structure may be rotatably moveable around a central vertical axis, enabling specimens to be loaded onto and unloaded from the second structure at a chosen position alongside the apparatus, either by a robotic arm or a human hand.

The apparatus may have the facility to change the liquid when in the first position, enabling the specimens to be treated by different liquids in a succession of treatment stages, whilst retaining the chamber closed. For example, the apparatus may have a pump to fill and empty the chamber with a succession of chosen liquids which, in the case of tissue specimens, may act to wash or otherwise treat the specimens prior to the specimens being imaged by means of optical projection tomography.

According to another aspect of the invention there is provided a method of treating tissue specimens by immersion in a liquid in a chamber, the method comprising loading the specimens onto a holder so that the specimens depend from the holder and are disposed above the liquid in the chamber, effecting relative movement between the chamber and the specimens in one direction to cause immersion of the specimens in the liquid whilst maintaining the chamber closed and protected from the environment during immersion, effecting relative movement between the chamber and the specimens in the opposite direction to bring the specimens out of the liquid, and unloading the treated specimens from the holder.

The specimens may be treated by different liquids in a plurality of treatment stages which are preferably carried out by successive emptying and filling of the chamber with the different liquids, whilst the specimens remain in the chamber and whilst the chamber remains closed and protected from the environment.

According to another aspect of the present invention, there is provided a method of performing any one or more of the analyses or procedures listed hereunder comprising use of a method or apparatus of any of the aspects set out above.

According to the present invention, samples for use in the present invention may be prepared as described in the earlier patent applications and/or employing conventional pathological and histological techniques and procedures well known to persons skilled in the art.

For example, in-situ hybridisation (particularly useful for detecting RNAs): Hammond K L, Hanson I M, Brown A G, Lettice L A, Hill R E "Mammalian and Drosophila dachsund genes are related to the Ski proto-oncongene and are expressed in eye and limb". Mech Dev. 1998 June; 74(1-2): 121-31.

Immunohistochemistry (particularly useful for detecting proteins and other molecules): Sharpe J, Ahlgren U, Perry P, Hill B, Ross A, Hecksher-Sorensen J, Baldock R, Davidson D. "Optical projection tomography as a tool for 3D microscopy and gene expression studies" Science. 2002 Apr. 19; 296(5567):541-5.

It will be appreciated that modification may be made to the invention without departing from the scope of the invention.

BRIEF DESCRIPTION OF THE DRAWINGS

The invention will now be further described, by way of example, with reference to the accompanying drawings, in which:—

DETAILED DESCRIPTION

Figure 1:
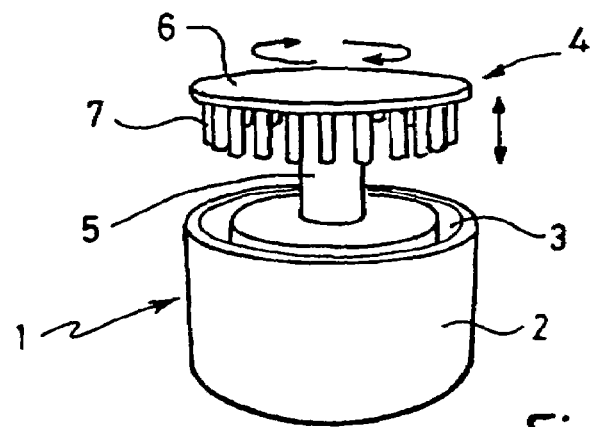
FIG. 1 is an isometric view of apparatus according to the invention and in an open condition.

The apparatus comprises a fixed structure 1 having a cylindrical outer casing 2 in the top of which is positioned an annular trough 3 which is open at the top. Mounted in the fixed structure is a moveable structure 4 having a central hub or spindle 5 on the top of which is mounted a disc-like lid 6 the underside of which carries a number of angularly spaced and downwardly depending cylindrical magnets 7. The hub or spindle 5 is rotatably mounted in the fixed structure for rotation of the moveable structure about a central vertical axis indicated at 8 in FIG. 4. Also, the hub or spindle 5 is capable of vertical translational movement with respect to the fixed structure 1 along the vertical axis 8.

Figure 4:
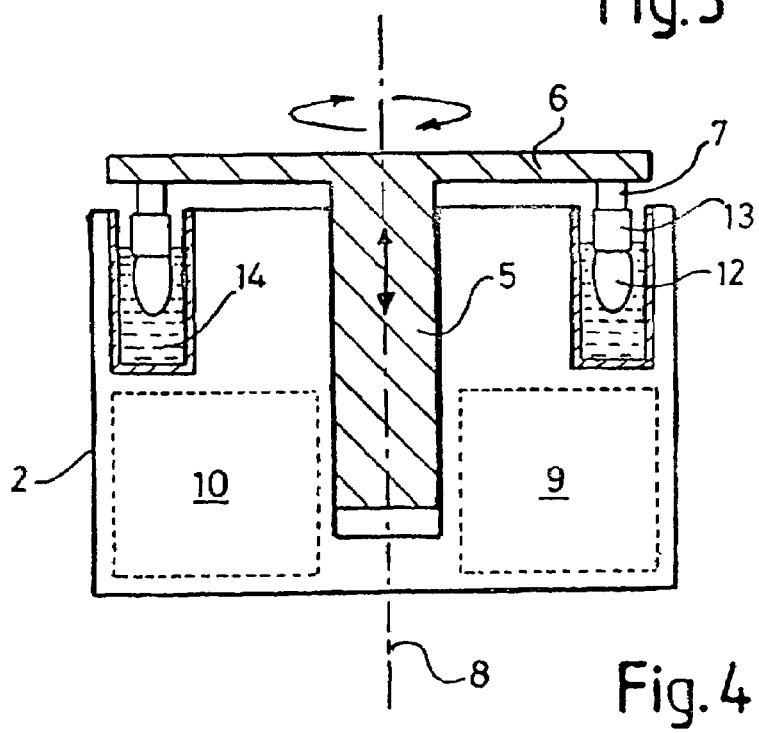
FIG. 4 is a cross-sectional view of the apparatus.
Figure 5:
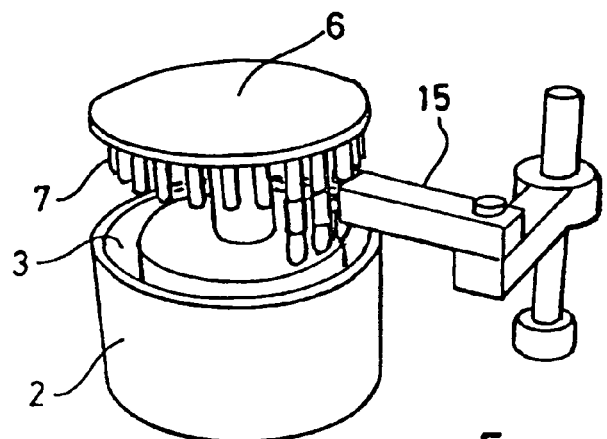
FIG. 5 shows the apparatus in combination with a robotic arm.

Within the casing 2 are located motors and gearing for driving the structure 4 both in rotation and translational movement, as indicated at 9 in FIG. 4. The trough 3 is capable of being filled with liquids, and the structure 1 includes containers for holding these liquids and pumps for filling and emptying the trough, as indicated at 10 in FIG. 4.

Figure 2:
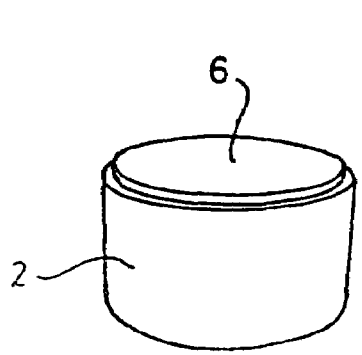
FIG. 2 is an isometric view of the apparatus in a closed condition.
Figure 3:
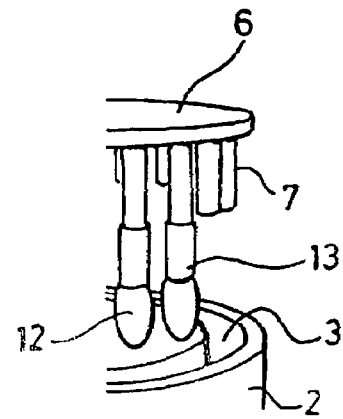
FIG. 3 is a fragmentary view, to an enlarged scale, of part of the apparatus in an open condition, showing specimens held by the apparatus.

The magnets 7 are used to hold, in a detachable manner, tissue specimens 12 each of which has been prepared with a metal mount 13 at one end of the specimen. This allows each metal 13 mount to depend from one of the magnets 7, with the specimen 12 depending downwardly from the mount 13. When the apparatus is in the open condition (FIG. 1), the magnets 7 are raised clear of the top of the trough 3 so that the specimens 12 can be attached to or removed from the magnets 7. When the apparatus is in the closed position (FIG. 2), the lid 6 engages the top of the casing 2 and the specimens 12 are immersed in a liquid 14 in the trough 3.

Figure 6:
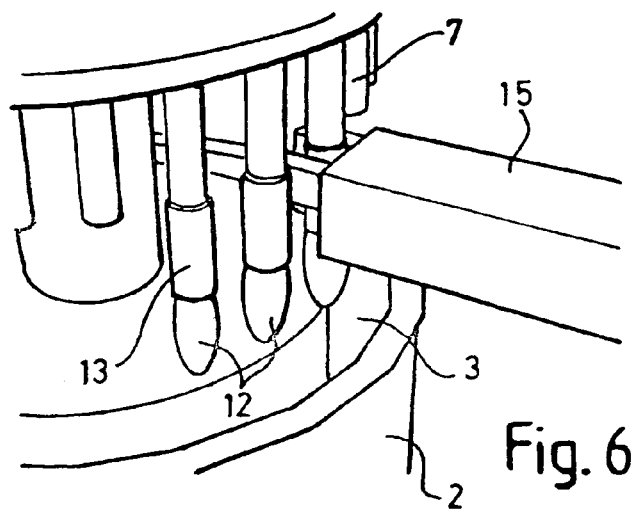
FIG. 6 is an enlarged view of part of FIG. 5.
Figure 7:
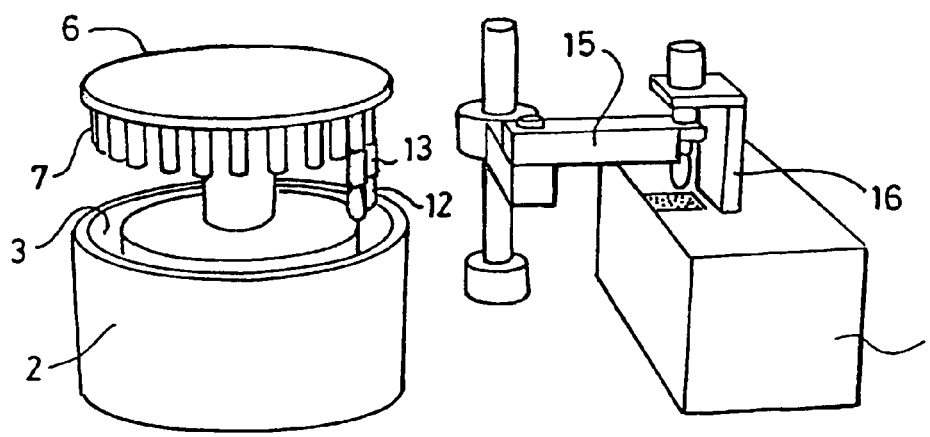
FIG. 7 shows the robotic arm positioning a specimen onto the rotary stage of an OPT scanner.

The robotic arm 15 shown in FIGS. 6 and 7 is used to load untreated specimens into the apparatus and also to transfer treated specimens from the apparatus to the rotary stage 16 of an OPT scanner where the specimens are imaged.

In use, the robotic arm 15 is used to load specimens into the apparatus, each specimen being attached to the lower end of a corresponding magnet 7 by virtue of the magnetic attraction between the magnet 7 and the metal mount 13 at one end of the specimen 12, the moveable structure 4 being in the open position and being indexed in a rotational sense as the specimens are loaded. When loaded with specimens, the moveable structure is moved to its lowered or closed position, thereby immersing the specimens 12 in the liquid 14 which has been pumped into the trough 3. In this closed position, the lid 6 engages the upper rim of the outer casing 2 so that the liquid 14 is closed to the air, thereby allowing the use of a volatile liquid, unlike known apparatus which uses conveyor belts for transferring specimens through a liquid.

If it is required to treat the specimens by a succession of liquids, the first liquid is drained from the trough 3 and a second liquid pumped thereinto, without the need for the trough 3 to be opened to the air. Moreover, the attachment of the metal mounts 13 to the magnets 7 retains the specimens 12 in their hanging positions so that the specimens do not engage the bottom of the trough 3, which could damage them.

Any number of treatment stages can be carried out in this manner, the liquid being changed without the need to move the specimens and employing only a small volume of each treatment liquid.

After treatment of the specimens 12, the moveable structure 4 is raised to its upper position and the treated specimens 12 are then transferred to the rotary stage 16 by means of the robotic arm 15, the structure 4 being rotationally indexed to enable the robotic arm 15 to unload each specimen 12 in turn and to transfer the treated specimen 5 to the rotary stage 16.

Examples of liquids for treating the specimens are fixatives (such as paraformaldehyde or formalin), alcohols (in particular methanol and ethanol) and organic solvents for clearing the specimens (in particular benzyl alcohol and benzyl benzoate).

It will be appreciated that modification may be made to the invention without departing from the scope of the invention.

The invention claimed is:

1. Apparatus for treating a plurality of tissue specimens by immersion in a common liquid, the apparatus comprising a first structure providing a chamber for holding the liquid, and a second structure including a plurality of holding means for releasably holding the plurality of specimens, the first and second structures being relatively moveable in a direction having a vertical component between a first position in which the holding means are relatively close to the chamber and in which the second structure closes the top of the chamber to enable the plurality of specimens to be immersed in the common liquid whilst the latter is protected from the environment, and a second position in which the holding means are relatively distant from the chamber to enable the plurality of specimens to be loaded onto or unloaded from the holding means, and further in which the chamber is in the form of an annular trough; the plurality of holding means hold the plurality of specimens so that the latter depend from their respective holding means at angularly spaced positions around a circle for immersion in the annular trough containing the common liquid; and the second structure includes a lid which acts to close the chamber in the first position and the underside of which carries the holding means.

2. Apparatus according to claim 1, wherein the first structure is stationary and the second structure is shiftable vertically with respect to the first structure.

3. Apparatus according to claim 1 or 2, wherein the holding means include magnets to enable specimens, each provided with a metal mount, to be detachably retained on the second structure by magnetic attraction.

4. Apparatus according to claim 1, wherein the second structure is rotatably moveable around a central vertical axis, enabling specimens to be loaded onto and unloaded from the second structure at a chosen position alongside the apparatus, either by a robotic arm or a human hand.

5. Apparatus according to claim 1, wherein the apparatus is further composed of a device to change the common liquid when in the first position, enabling the specimens to be treated by different common liquids in a succession of treatment stages, whilst retaining the chamber closed.

* * * * *